(12) United States Patent
Tsengas

(10) Patent No.: US 9,125,401 B1
(45) Date of Patent: Sep. 8, 2015

(54) EVAPORATIVE GEL DELIVERY OF CATNIP AROMA

(71) Applicant: OurPet's Company

(72) Inventor: Steven Tsengas, Fairport Harbor, OH (US)

( * ) Notice: Subject to any disclaimer, the term of this patent is extended or adjusted under 35 U.S.C. 154(b) by 58 days.

(21) Appl. No.: 14/207,873

(22) Filed: Mar. 13, 2014

Related U.S. Application Data

(60) Provisional application No. 61/781,550, filed on Mar. 14, 2013.

(51) Int. Cl.
*A01K 15/02* (2006.01)
*A01K 29/00* (2006.01)
*A01N 25/18* (2006.01)
*A01N 25/04* (2006.01)

(52) U.S. Cl.
CPC .............. *A01N 25/18* (2013.01); *A01K 15/025* (2013.01); *A01N 25/04* (2013.01)

(58) Field of Classification Search
CPC ......... A61L 9/048; A61L 9/042; A61L 9/012; A01N 37/18; A01N 37/40; A01N 49/00; A01N 65/00; A01N 65/22; A01N 65/24; A01N 65/36; A01N 25/10; A01N 25/18; A01N 25/006; A01K 15/025
USPC ................ 119/711, 702, 707, 709, 710, 174; 424/76.3, 76.4
See application file for complete search history.

(56) References Cited

U.S. PATENT DOCUMENTS

| | | | | |
|---|---|---|---|---|
| 3,956,173 A | * | 5/1976 | Towle | 516/107 |
| 3,969,280 A | * | 7/1976 | Sayce et al. | 512/4 |
| 3,997,480 A | * | 12/1976 | Singleton et al. | 512/4 |
| 4,056,612 A | * | 11/1977 | Lin | 424/76.3 |
| 4,071,616 A | * | 1/1978 | Bloch | 424/76.4 |
| 4,128,507 A | * | 12/1978 | Mitzner | 512/4 |
| 4,178,264 A | * | 12/1979 | Streit et al. | 516/107 |
| 4,755,377 A | * | 7/1988 | Steer | 424/76.4 |
| 4,809,912 A | * | 3/1989 | Santini | 239/60 |
| 4,928,632 A | * | 5/1990 | Gordon | 119/709 |
| 5,034,222 A | * | 7/1991 | Kellett et al. | 424/76.4 |
| 5,698,188 A | * | 12/1997 | Evans | 424/76.4 |
| 5,741,482 A | * | 4/1998 | Modi | 424/76.3 |
| 6,060,039 A | * | 5/2000 | Roe et al. | 424/9.2 |
| 6,517,856 B1 | * | 2/2003 | Roe et al. | 424/410 |
| 8,679,469 B2 | * | 3/2014 | Allison et al. | 424/76.4 |
| 2012/0230936 A1 | * | 9/2012 | Mikkelsen | 424/76.4 |
| 2012/0308512 A1 | * | 12/2012 | Albee et al. | 424/84 |

* cited by examiner

*Primary Examiner* — Yvonne Abbott-Lewis
(74) *Attorney, Agent, or Firm* — John D Gugliotta

(57) ABSTRACT

A pet toy in provided in combination with a material for the evaporative delivery of catnip aroma. The evaporative material comprising substantially catnip oil, sunflower oil, and polyacrylamide, wherein the catnip oil and/or the sunflower oil are delivered by evaporation through syneresis. A number and size of openings in the pet toy housing are varied as desired to control the rate at which odor is allowed to permeate, and the amount of evaporative gel or rate of syneresis can control the duration through which the odors may be attractive to pets.

20 Claims, 5 Drawing Sheets

EVAPORATIVE GEL DELIVERY OF CATNIP AROMA

RELATED APPLICATIONS

The present application claims benefit of U.S. Provisional Application 61/781,550, filed on Mar. 14, 2013, and is incorporated by reference as if fully rewritten herein.

BACKGROUND OF THE INVENTION

1. Field of the Invention

The present invention relates generally to small animal litter boxes and, more particularly, to an absorbent, disposable litter may and related products for use in conjunction with pet waste absorbent litter.

2. Description of the Related Art

There are many pet toys available that provide entertainment to the pet and the owner, including pet toys that dispense treats upon rolling or movement of the toy. Also well known in the art are pet toys that are used to engage a pet in physical activity that employ the use of aromas or scents as attractants or enhancements of the toy. These include the use of stuffed toys having catnip embedded therein. However, because the delivery of aromatic attractants such as catnip require evaporation of the key ingredients to be effective, the efficacy of such attractants are inevitably limited to short durations. As such, these toys often provide for the replenishment of catnip, either in the form of solid or liquid extract, into or within the toy for subsequent dispensing based on movement or rotation of the toy or its interaction with the surrounding air. The present invention is markedly different by providing for extended delivery of an effective rate of aromatic compounds efficacy. This, among other disclosed advantages and features, overcome many of the deficiencies outlined and inherent within the known prior art.

A search of the prior art did not disclose any patents that read directly on the claims of the instant invention; however, the following references were found that deal with evaporative delivery of other active agents and, to this extent, were considered related.

U.S. Pat. No. 2,691,615 (1954, Turner, et al.) is a very early reference claiming a gel based air freshener. The reference discloses the use of agar-agar, gelatin, pectin, starch, and various gums as potential gelling agents for forming air conditioning gels. The aqueous air treating gel comprised of volatile air treatment compounds, water, and 1 to 4% of an aqueous gelling agent, (preferably agar-agar or calcium alginate), was found to be firm and substantially devoid of syneresis.

U.S. Pat. No. 2,927,055 (1960, Lanzet) discloses an air-treating gel comprising water, a volatile air treatment component, and a gelling agent mixture comprising carrageenan, Locust Bean gum, potassium chloride, and sodium carboxymethyl cellulose. The mixture is blended at around 170° F., then poured into molds and cooled. The inventors successfully balanced the amounts of these components to improve the viscosity/handling of the gel in the hot/molten state and to optimize stability, firmness, and appearance of the solidified gel.

U.S. Pat. No. 4,056,612 (1977, Lin) discloses an air freshener gel that utilizes a gelling agent mixture comprising carrageenan (mostly kappa and lambda), Locust Bean gum, and an ammonium salt. The inventive gels exhibited high water gel strengths and syneresis rates of less than 0.3%.

U.S. Pat. No. 4,178,264 (1979, Streit, et al.) discloses an improved air-treating gel composition comprising both carrageenan and a stearate salt used in combination as the gelling agent, wherein the preferred ratio of carrageenan to stearate is from about 0.3:1 to about 5:1. In addition to carrageenan, stearate, water, and volatile actives, a stearate solubility enhancer, such as a solvent or one of a variety of nonionic materials, to increase the solubility of the stearate in the aqueous environment. The preferred components for enhancing the stearate solubility include ethylene glycol, propylene glycol, and ethanol. Most of the Streit example compositions comprise propylene glycol, carrageenan, and sodium stearate combinations for rigid and stable gels.

U.S. Pat. No. 4,666,671 (1987, Purzycki, et al.) discloses fragranced gel blocks useful for deodorizing urinals and toilet bowls. These gel blocks comprise a gelling agent selected from fatty acid salts, sodium alginate, carboxymethyl cellulose, carrageenan, hydroxypropyl cellulose, starches, and gums, although the most preferred gelling agent disclosed is sodium stearate used alone. Solvents including lower alkyl alcohols, diols, and glycol ethers are optionally added to adjust the final melting temperature range of the gel block.

U.S. Pat. No. 5,643,866 (1997, Ansari, et al.) discloses an air-treating gel comprising dibenzylidene sorbitol acetal (DBSA) in combination with a glycol component as the aqueous gelling agent mixture. Such air freshener gels comprising fragrance, water, DBSA and glycol are shaped solid gel products that can withstand temperatures up to 50/-60/C. without melting.

U.S. Pat. No. 5,698,188 (1997, Evans) discloses a gel air fragrancing composition comprising carrageenan in accordance with Lanzet '055. The preferred compositions of Evans comprise 1-20% fragrance, 2-10% carrageenan constituent, and optional preservative and coloring agents, with the balance being water. The carrageenan constituents include commercial thickeners based on carrageenan that are likely to also include proprietary amounts of other materials such as Locust Bean gum, cellulose materials and calcium and/or potassium salts.

U.S. Patent Application Publication 2008/0317683 (2008, Trudso) discloses carrageenan compositions and products containing these compositions. The disclosure is directed to methods for extracting and producing carrageenans having a mixture of counter-ions (sodium, potassium, calcium and magnesium), wherein the carrageenan composition has a gelling temperature of between 7° C. and 30/C. An air freshener gel is disclosed that comprises the carrageenan composition having the optimized mixture of cations.

And lastly, U.S. Patent Application Publication 20120/230936 (2012, Mikkelsen) discloses a solid and self-standing carrageenan gel air freshener composition that exhibits slowed evaporation and extended length-of-life made possible by the addition of relatively small amounts of extenders consisting of C14-C18 fatty alcohols.

Consequently, a need has been felt for providing the extended delivery of aromatic attractant for encouraging pet interaction wherein the aromatic oil extract(s) is delivered through syneresis to effectively extend the amount of time an attractant odor is available.

SUMMARY OF THE INVENTION

Therefore, it is an object of the present invention to provide a pet toy for delivery of olfactory attractant.

It is another object of the present invention to provide for such a toy where the attractant is derived from or related to catnip It is yet another object of the present invention to provide a toy where the attractant is available in an evaporative gel form.

As described in one embodiment of the present invention, a pet toy is provided including the extended delivery of aromatic attractant for encouraging pet interaction. The shape of the toy is adapted for the metered delivery of airborne attractant, such as, for example, improved adaptations of existing catnip delivery toys including a catnip ball such as a Play-N-Treat® ball as sold by OurPet's Company of Fairport, Ohio. Other shapes, such as egg shapes, stars, mice, fish, etc. are further anticipated as being capable of operating in concert with the present teachings.

A major functional element of the toy, whatever housing design is provided, should be that the housing can be opened to facilitate the placing of gel inside. Fluid communication between the interior cavity and the exterior atmospheres, such as through holes or other openings in the housing, allow the aromatic attractant to be dispensed into the area to entice the cat or other target pet.

The attractant may provide for an all natural oil based entrained in an appropriate aqueous gel or non-aqueous type of gel. Specifically, the preferred non-aqueous type of gel that accommodates a formulation of all natural ingredients (with percentages being by weight) includes:
  a. Olfactory attractant Natural Oil (catnip oil, honeysuckle, valerian, salmon oil, tuna oil, etc.)—approximately 0.2-2.0%;
  b. Natural oil (sunflower oil, cannola oil, olive oil, etc.)—approximately 13-14%;
  c. Natural based gel carrier (shea butter, etc.)—approximately 84-84.9%
  d. Phoenoxyethanol (natural preservative)—approximately 0.1%

In addition to the aqueous and Shea butter gels, it is felt that gels made of polyacrylamide gel can also provide sufficient delivery and evaporation through syneresis to be effective.

An advantage in the use of such an all natural based treat is that the owner and pet will make contact and enhance bonding while cat your enjoys licking the treat. Additionally, the cat's health may be enhanced since:
  a. The Sunflower Oil is rich in Vitamin E (natural anti-oxidant to reduce cell damage from free radicals), is a natural moisturizer that helps retain water in cells, is rich in Vitamin B (important for a healthy nervous system and digestion), rich source of Zinc (enhances healing and a keen sense of smell and taste) and Folic Acid (enhances healthy cell growth and reproduction); and
  b. The Shea Butter is derived from the Karite Tree (Tree of Life) and is rich in the anti-oxidant vitamins A and E. It also contains various essential fatty acids (conducive to healthy skin and overall healing) and Cinnamic Acid (effective anti inflammation and prevention of tumor development).

In summary, the All-Natural gel can be sold both as a "feline scent provider" as well as a "healthy feline treat".

The foregoing and other aspects will become apparent from the following detailed description of the invention when considered in conjunction with the accompanying drawing figures.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

It should be understood that the pet interactive pet toy can be adapted to various designs, including shapes such as egg shapes, stars, mice, fish, etc., and that the present disclosure is intended to describe preferred embodiments of the present invention.

DESCRIPTION OF THE PREFERRED EMBODIMENTS

The best mode for carrying out the invention is presented in terms of its preferred embodiment, herein depicted within the Figures.

1. Detailed Description of the Figures

Before explaining the present invention in detail, it is important to understand that the invention is not limited in its application to the details of the construction illustrated and the formulations described herein. The invention is capable of other embodiments and of being practiced or carried out in a variety of ways. It is to be understood that the phraseology and terminology employed herein is for the purpose of description and not of limitation.

Figure 1:
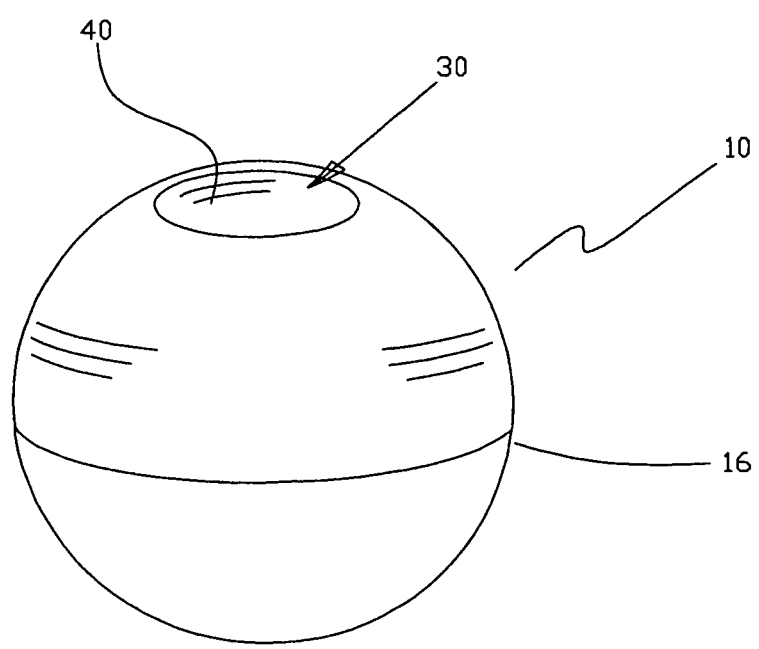
FIG. 1 is a perspective view of an interactive pet toy for the evaporative delivery of catnip aroma according to the preferred embodiment of the present invention shown in a closed condition.

In the following detailed description of a first preferred embodiment and a second preferred embodiment of the present invention, reference is made to the accompanying drawings which, in conjunction with this detailed description, illustrate and describe a first preferred embodiment and a second preferred embodiment of a pet toy ball feeder in accordance with the present invention. Referring now to the drawings, in which like-referenced characters represent corresponding elements throughout the several views, attention is first directed to FIG. 1 and FIG. 2, which illustrate an interactive pet toy ball for the evaporative delivery of catnip aroma according to the preferred embodiment of the present invention, generally identified by reference number 10. Pet toy ball includes first hollow semi-spherical half member 12 and second semi-spherical half member 14 brought together at seam 16. Pet toy ball feeder 10 is intended for use by pets, such as cats, dogs, ferrets, rabbits and hamsters, and thus pet toy ball feeder 10 is manufactured to withstand substantial force from such pets without breaking. This is preferably achieved by increasing wall thickness 18 and manufacturing first hollow semi-spherical half member 12 and second hollow semi-spherical half member 14 from a material that can withstand substantial forces such as polycarbonate, polyvinyl chloride, rubber or other plastic or polymer materials known in the art as accomplishing the purposes of the invention. The pet toy ball 10 can be manufactured in different diameters in a range of, for example, from one (1) inch to twelve (12) inches to accommodate the differences in size among pets. In addition, pet toy ball feeder 10 can be made in a variety of colors, including clear, opaque and translucent colors. The preferred diameter of pet toy ball feeder 10 to be used by cats, small dogs, ferrets and rabbits is approximately two (2) inches and pet toy ball feeder 10 is preferably fabricated from a translucent material.

Figure 2:
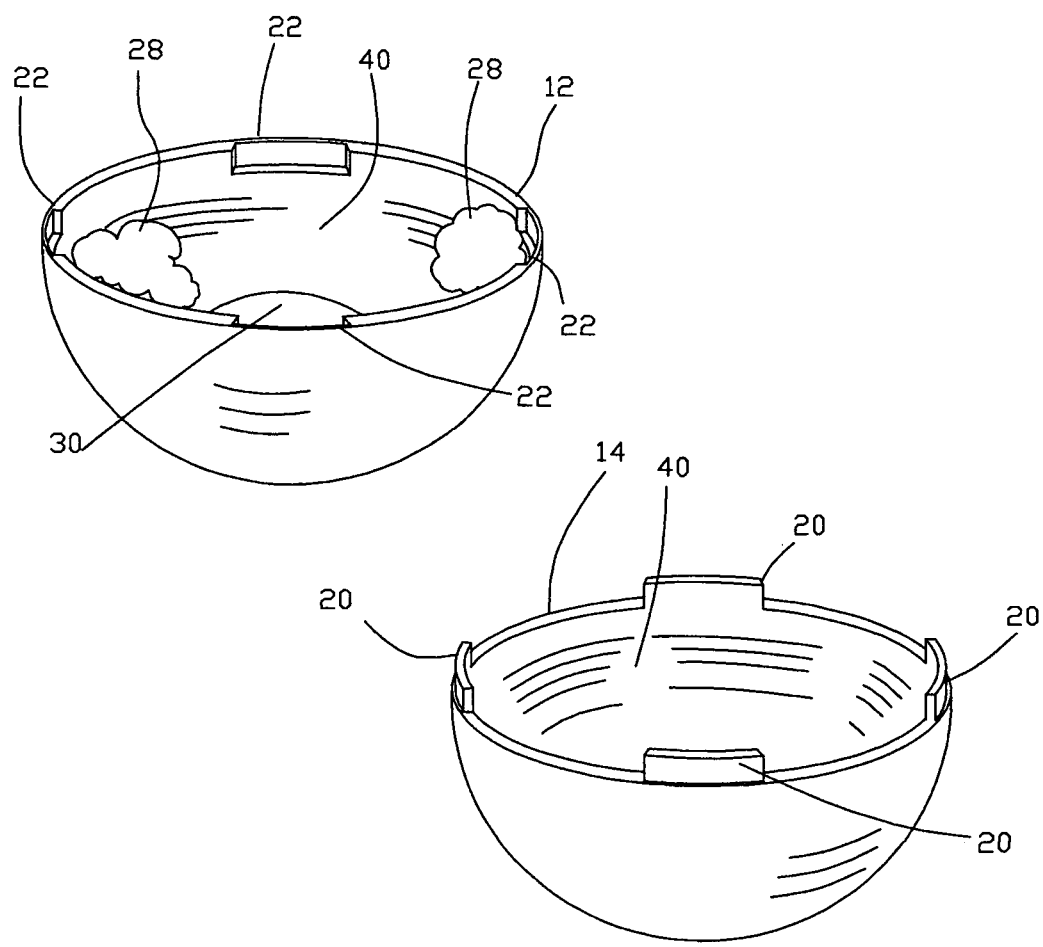
FIG. 2 is a perspective view of the interactive pet toy of FIG. 1, shown in an open condition.

As shown in greater detail in FIG. 2, one or both of first hollow semi-spherical half member 12 and second semi-spherical half member 14, includes one (1) or more, and more preferably two (2) or more, resilient flexible projections 20 extending outwardly from seam 16. Resilient flexible projections 20 correspond to, and are resiliently received in, one or more grooves 22, and most preferably a continuous groove around the circumference of the other of one or both of the first hollow semi-spherical half member 12 and second semi-spherical half member 14, to retain first hollow semi-spherical half member 12 and second hollow semi-spherical half member 14 in a spherical ball configuration. An evaporative gel odor attractant 28, as described in greater detail below, is preferably placed inside pet toy ball feeder 10 prior to snapping first hollow semi-spherical half member 12 and second hollow semi-spherical half member 14 together into its spherical ball configuration.

The pet toy ball 10 also includes one or more openings 30 through first hollow semi-spherical half member 12 and/or second hollow semi-spherical half member 14. The one or more openings 30 preferably provide free fluid communication between a cavity 40 formed inside the ball 10 and the surrounding environment such that volatile and/or aromatic compounds can freely permeate from within the inner cavity 40.

In addition, for cats in particular, catnip oil emanating through syneresis from within an evaporative gel odor attractant 28 can be placed with or replace in pet toy ball 10 to provide a catnip odor which will further stimulate the cat. Furthermore, the number and size of one or more openings 30 can be varied as desired to control the rate at which odor is allowed to permeate, and the amount of evaporative gel or rate of syneresis can control the duration through which the odors may be attractive to pets.

Figure 3:
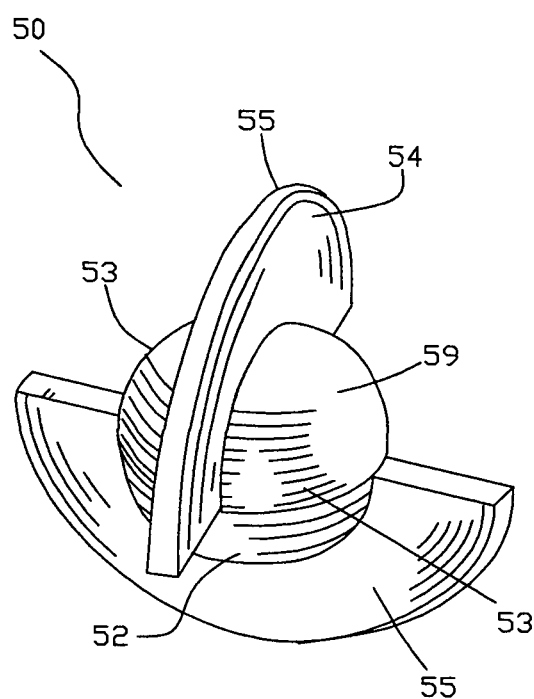
FIG. 3 is a perspective view of an interactive pet toy for the evaporative delivery of catnip aroma according to the an alternate preferred embodiment of the present invention shown in a closed condition.
Figure 4:
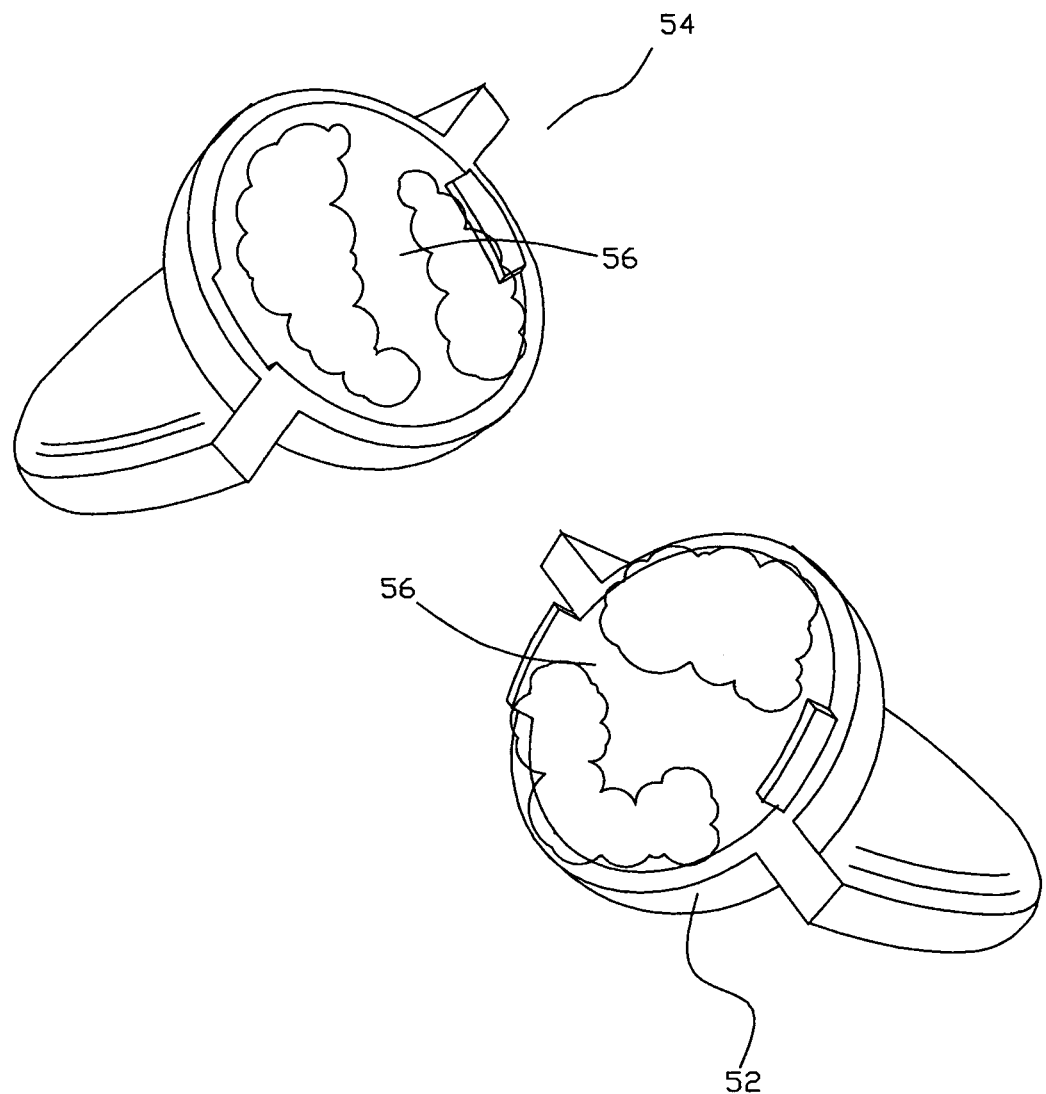
FIG. 4 is a perspective view of the interactive pet toy of FIG. 3, shown in an open condition.
Figure 5:
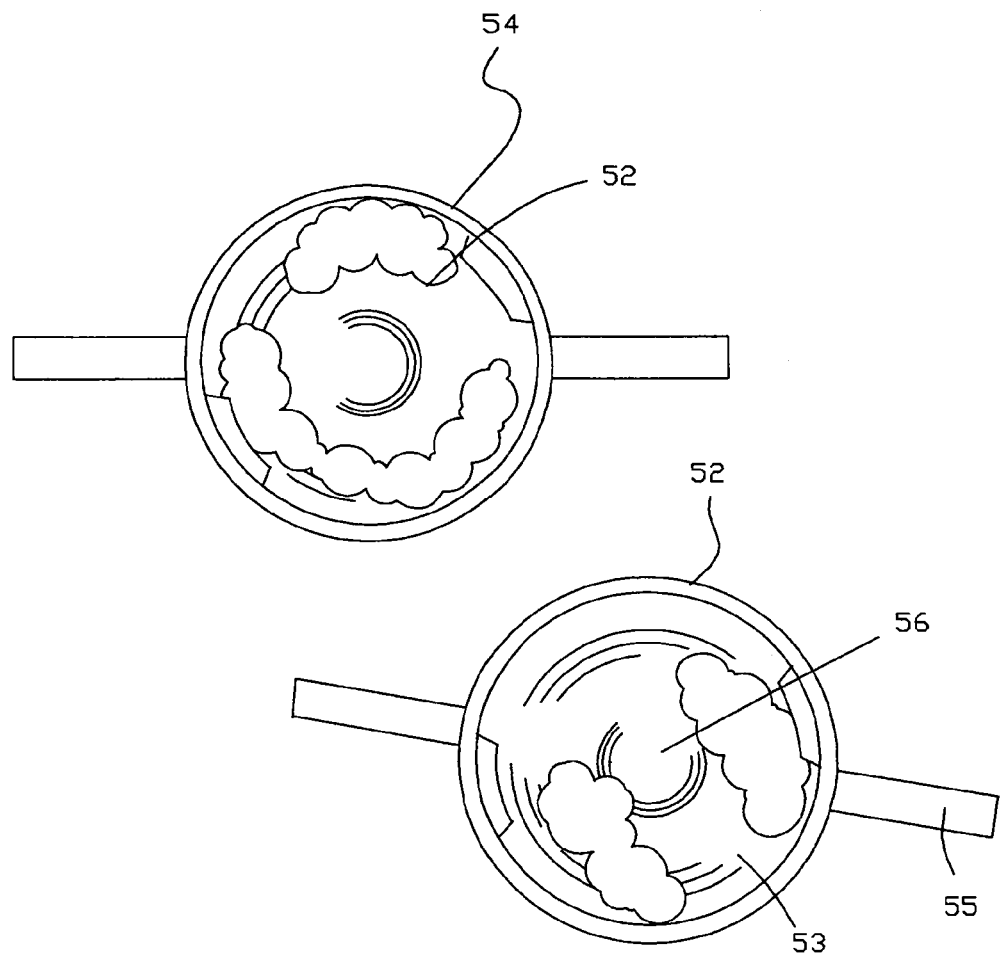
FIG. 5 is a front plan view thereof.

Referring now to FIGS. 3-5, and interactive pet toy for the evaporative delivery of catnip aroma according to the an alternate preferred embodiment of the present invention shown in which the housing 50 comprises a first component 52 coupled to a second component 54. The first component and the second component form an internal space 56 for retaining the evaporative gel odor attractant 28, as described in greater detail below. The first component and the second component have a plurality of apertures 58 in fluid communication with the internal space 56 and the evaporative gel odor attractant 28 retained therein. The apertures 58 allow the scent, fragrance or odor to externally escape so that a feline or felines can smell the scent provided.

As generally depicted in FIG. 3 through FIG. 5, the housing 50 may have several forms or geometries, including any polygonal shape or arrangement. In the embodiment depicted in the figures, the housing 50 has a first component 52 and a second component 54 that are mirror images of one another, so that a description of one component 52 or 54 serves as a representative description of the other remaining component 54 or 52. For example, as depicted, the first component 52 comprises a substantially hemispherical body 53 having a semi-circular fin 55 formed along an external surface of the body 53 and co-planar to a midline of the body 53. The fin 55 appears to divide the body 55 into two halves. The plurality of apertures 58 are formed along the surface of the body 53. Internally, the body 53 forms a bowl shape internal space 56 when coupled with the second component 53 (and the mirror image elements of the second component). Adjacent the bowl shape structure and on the perimeter of the body 53 are ridges or threads that engage teeth or extensions, and thus allow the first component 52 and second component 54 to securely couple together. The components 52 and 54 are turned or twisted in the opposite direction so as to achieve interference impingement of the teeth against the ridges is realized. When coupled, the components 52 and 54 are arranged so that the respective fins 55 are offset between 0° and 90°, with the offset preferably between 30° and 60°. The offset of the fins 55 provides the apparatus with the ability to wobble, spin or flutter when swatted by a feline during the course of play or engagement. It is envisioned that the components 52 and 54 may be of the same or different colors, with the preference of each component 52 and 54 having a different color to provide contrast and the illusion of movement to the apparatus during play.

A major functional element of the toy, whatever housing design is provided, should be that the housing can be opened to facilitate the placing of gel inside. Fluid communication between the interior cavity and the exterior atmospheres, such as through holes or other openings 58 in the housing, allow the aromatic attractant to be dispensed into the area to entice the cat or other target pet.

The attractant may provide for an aromatic attractant entrained in an appropriate aqueous gel or non-aqueous type of gel. Specifically, the preferred non-aqueous type of gel that accommodates a formulation of all natural ingredients includes:

a. Aromatic attractant—approximately between 0.2-2.0% by weight;
  b. Natural oil based thinning agent—approximately 13-14% by weight;
  c. Gel carrier—approximately 84-85% by weight; and
  d. Natural preservative—approximately 0.1% by weight.

The aromatic attractant may be any natural based oil, plant or extract that functions as an olfactory stimulant for pets, such as catnip, catnip oil, valerian, honeysuckle, salmon oil, tuna oil or the like. The oil based thinning agent may be any natural oil that functions to blend the aromatic attractant into the gel carrier, while at the same time allow for thinning and blending of the suspension sufficient to allow for gel dispensing. These oil based thinning agents may be sunflower oil, cannola oil, olive oil, or any natural based oil having similar physical properties. Such oils also have an additional benefit of being a source of various oil based vitamins in the even it is ingested.

It is anticipated that the gel carrier should be a natural based aqueous or shea butter gels, but it is felt that gels made of polyacrylamide gel can also provide sufficient delivery and evaporation through syneresis to be effective. In its preferred embodiment an all natural preservative can be phoenoxyethanol or similar material.

2. Operation of the Preferred Embodiment

In operation, the present invention is a reactive pet toy as already displayed in the applicant's own prior art, substantially as shown and described in U.S. Pat. No. 6,237,538 and U.S. Pat. No. 7,926,450, but includes the additional interactive features of utilizing, in combination, an evaporative gel odor attractant placed with or replaced inside to provide a catnip odor which will further stimulate the cat. The amount of evaporative gel or rate of syneresis of catnip oil to the diluent can control the duration through which the odors may be attractive to pets. In this manner the pet can be stimulated to begin playing with the pet toy in a similar manner as the pet is stimulated to continue playing with the pet toy for an extended duration, well past that of conventionally available catnip containing toys. In addition, an aromatic olfactory attractant suspended into an evaporative gel, all made with natural ingredients and thinned such as capable of being delivered as a gel, cream or paste can have other applications, such as, for example, an edible "treat" that can be applied directly to a toy or carrier or directly to a pet owner's finger or hand to encourage pet bonding through 'licking' or similar action. In addition, such a composition, being made of natural ingredient all of which may be generally regarded as safe, can be a source of vitamins and other nutrients.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

What is claimed is:

1. A solid or gel material for use as an attractant for a pet toy comprising:
    a. Aromatic attractant—approximately between 0.2-2.0% by weight;
    b. Natural oil based thinning agent—approximately 13-14% by weight;
    c. Gel carrier—approximately 84-85% by weight; and
    d. Natural preservative—approximately 0.1% by weight;
wherein said solid or gel material provide sufficient delivery and evaporation of said aromatic attractant through syneresis to be effective.

2. The material of claim 1, wherein said aromatic attractant is selected from the group consisting of any natural based oil, plant or extract that functions as an olfactory stimulant for pets.

3. The material of claim 2, wherein said aromatic attracting is selected from the group consisting of: catnip; catnip oil; valerian; honeysuckle; salmon oil, and tuna oil.

4. The material of claim 1, wherein said oil based thinning agent comprises any natural oil that functions to blend the aromatic attractant into the gel carrier, while at the same time allow for thinning and blending of a suspension sufficient to allow for gel dispensing.

5. The material of claim 4, wherein said oil based thinning agents is selected from the group consisting of: sunflower oil; cannola oil; and olive oil.

6. The material of claim 1, wherein said gel carrier comprises a natural based aqueous, shea butter, or polyacrylamide gel.

7. The material of claim 1, wherein said all natural preservative comprises phoenoxyethanol.

8. A pet toy in combination with the solid or gel material of claim 1 for extended delivery of aromatic attractant from said pet toy for encouraging pet interaction.

9. The combination of claim 8, wherein said pet toy a pet toy further comprises:
    a housing having a first hollow semi-spherical half member and second semi-spherical half member brought together at seam and thereby forming an inner volume;
    an inner volume for containment and delivery of said solid or gel material for evaporative odor delivery; and
    at least one opening formed through said first hollow semi-spherical half member for providing free fluid communication between said inner volume and the surrounding environment such that volatile and/or aromatic compounds can freely permeate from within the inner volume.

10. The combination of claim 8 further comprising at least one resilient, flexible projections from at least said first hollow semi-spherical half member extending outwardly from said seam.

11. An interactive pet toy for the evaporative delivery of catnip aroma comprising:
    a pet toy housing having a first hollow semi-spherical half member and second semi-spherical half member brought together at seam and thereby forming an inner volume;
    an evaporative gel odor attractant retainable within said inner volume; and
    at least one opening formed through said first hollow semi-spherical half member for providing free fluid communication between said inner volume and the surrounding environment such that volatile and/or aromatic compounds can freely permeate from within the inner volume;
wherein said evaporative gel odor attractant provides a catnip odor for stimulating a cat.

12. The interactive pet toy of claim 11, wherein said evaporative gel odor attractant comprises a formulation comprising:
    a. Aromatic attractant—approximately between 0.2-2.0% by weight;
    b. Natural oil based thinning agent—approximately 13-14% by weight;
    c. Gel carrier—approximately 84-85% by weight; and
    d. Natural preservative—approximately 0.1% by weight;
wherein said solid or gel material provide sufficient delivery and evaporation of said aromatic attractant through syneresis to be effective.

13. The interactive pet toy of claim 12 wherein said aromatic attractant is selected from the group consisting of any natural based oil, plant or extract that functions as an olfactory stimulant for pets.

14. The interactive pet toy of claim 13, wherein said aromatic attractant is selected from the group consisting of: catnip; catnip oil; valerian; honeysuckle; salmon oil, and tuna oil.

15. The interactive pet toy of claim 11, wherein said oil based thinning agent comprises any natural oil that functions to blend the aromatic attractant into the gel carrier, while at the same time allow for thinning and blending of a suspension sufficient to allow for gel dispensing.

16. The interactive pet toy of claim 15, wherein said oil based thinning agents is selected from the group consisting of: sunflower oil; cannola oil; and olive oil.

17. The interactive pet toy of claim 11, wherein said gel carrier comprises a natural based aqueous, shea butter, or polyacrylamide gel.

18. The interactive pet toy of claim 11, wherein said all natural preservative comprises phoenoxyethanol.

19. The interactive pet toy of claim 11, further comprising at least one resilient, flexible projections from at least said first hollow semi-spherical half member extending outwardly from said seam.

20. In combination:
    a pet toy adapted for the evaporative delivery of catnip aroma having a housing forming an accessible inner containment volume and further forming at least one opening in said housing; and
    an evaporative material comprising substantially catnip oil, sunflower oil, and polyacrylamide;

wherein the catnip oil and/or the sunflower oil are delivered by evaporation through syneresis; and wherein a number and size of said at least one opening can be varied as desired to control the rate at which odor is allowed to permeate, and the amount of evaporative gel or rate of syneresis can control the duration through which the odors may be attractive to pets.

\* \* \* \* \*